United States Patent
Al-Ali et al.

(10) Patent No.: US 8,920,317 B2
(45) Date of Patent: *Dec. 30, 2014

(54) MULTIPURPOSE SENSOR PORT

(71) Applicant: Masimo Corporation, Irvine, CA (US)

(72) Inventors: Ammar Al-Ali, San Juan Capistrano, CA (US); Robert A. Smith, Lake Forest, CA (US); Rex J. McCarthy, Mission Viejo, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/027,019

(22) Filed: Sep. 13, 2013

(65) Prior Publication Data

US 2014/0081097 A1    Mar. 20, 2014

Related U.S. Application Data

(63) Continuation of application No. 12/400,683, filed on Mar. 9, 2009, now abandoned, which is a continuation of application No. 10/898,680, filed on Jul. 23, 2004, now Pat. No. 7,500,950.

(60) Provisional application No. 60/490,091, filed on Jul. 25, 2003.

(51) Int. Cl.
*A61B 5/1455* (2006.01)
*A61B 5/00* (2006.01)
*A61B 5/024* (2006.01)
*G06F 19/00* (2011.01)

(52) U.S. Cl.
CPC ............ *A61B 5/14551* (2013.01); *A61B 5/0002* (2013.01); *G06F 19/3406* (2013.01); *A61B 5/02416* (2013.01); *A61B 2560/045* (2013.01); *A61B 2562/08* (2013.01)

USPC ............................. 600/300; 600/322; 600/323

(58) Field of Classification Search
CPC ............. A61B 5/1455; A61B 5/14551; A61B 2560/0443; A61B 2560/045; G06F 8/65; G06F 8/66; G06F 19/3406; G06F 19/3412
USPC ............................. 600/310, 322, 323; 702/189
See application file for complete search history.

(56) References Cited

U.S. PATENT DOCUMENTS

| 4,051,522 A | 9/1977 | Healy et al. |
| 4,216,462 A | 8/1980 | McGrath et al. |

(Continued)

FOREIGN PATENT DOCUMENTS

| DE | 19531520 | 1/1997 |
| EP | 0 019 478 A2 | 11/1980 |

(Continued)

OTHER PUBLICATIONS de Kock, J.P. et al., "The Effect of Varying LED Intensity on Pulse Oximeter Accuracy", *Journal of Medical Engineering & Technology*, vol. 15, No. 3, May/Jun. 1991, pp. 111-116.

(Continued)

*Primary Examiner* — Eric Winakur
(74) *Attorney, Agent, or Firm* — Knobbe Martens Olson & Bear LLP

(57) ABSTRACT

A sensor port is adapted to connect to either a sensor or a data source. A reader is configured to identify which of the sensor and the data source is connected to the sensor port. A data path is configured to communicate an analog signal associated with the sensor and digital data associated with the data source to a signal processor according to the identification made by the reader.

13 Claims, 11 Drawing Sheets

(56) References Cited

U.S. PATENT DOCUMENTS

| | | | |
|---|---|---|---|
| 4,237,344 | A | 12/1980 | Moore |
| 4,356,475 | A | 10/1982 | Neumann et al. |
| 4,674,085 | A | 6/1987 | Aranguren et al. |
| 4,887,260 | A | 12/1989 | Carden et al. |
| 4,916,444 | A | 4/1990 | King |
| 4,920,339 | A | 4/1990 | Friend et al. |
| 4,960,128 | A | 10/1990 | Gordon et al. |
| 4,964,408 | A | 10/1990 | Hink et al. |
| 5,038,800 | A | 8/1991 | Oba |
| 5,041,187 | A | 8/1991 | Hink et al. |
| 5,061,916 | A | 10/1991 | French et al. |
| 5,069,213 | A | 12/1991 | Polczynski |
| 5,126,648 | A | 6/1992 | Jacobs |
| 5,163,438 | A | 11/1992 | Gordon et al. |
| 5,319,355 | A | 6/1994 | Russek |
| 5,319,363 | A | 6/1994 | Welch et al. |
| 5,337,744 | A | 8/1994 | Branigan |
| 5,341,805 | A | 8/1994 | Stavridi et al. |
| D353,195 | S | 12/1994 | Savage et al. |
| D353,196 | S | 12/1994 | Savage et al. |
| 5,377,676 | A | 1/1995 | Vari et al. |
| D359,546 | S | 6/1995 | Savage et al. |
| 5,431,170 | A | 7/1995 | Mathews |
| D361,840 | S | 8/1995 | Savage et al. |
| D362,063 | S | 9/1995 | Savage et al. |
| 5,452,717 | A | 9/1995 | Branigan et al. |
| D363,120 | S | 10/1995 | Savage et al. |
| 5,456,252 | A | 10/1995 | Vari et al. |
| 5,479,934 | A | 1/1996 | Imran |
| 5,482,036 | A | 1/1996 | Diab et al. |
| 5,490,505 | A | 2/1996 | Diab et al. |
| 5,494,043 | A | 2/1996 | O'Sullivan et al. |
| 5,533,511 | A | 7/1996 | Kaspari et al. |
| 5,534,851 | A | 7/1996 | Russek |
| 5,561,275 | A | 10/1996 | Savage et al. |
| 5,562,002 | A | 10/1996 | Lalin |
| 5,564,108 | A | 10/1996 | Hunsaker et al. |
| 5,575,284 | A | 11/1996 | Athan et al. |
| 5,579,001 | A | 11/1996 | Dempsey et al. |
| 5,579,775 | A | 12/1996 | Dempsey et al. |
| 5,590,649 | A | 1/1997 | Caro et al. |
| 5,602,924 | A | 2/1997 | Durand et al. |
| 5,632,272 | A | 5/1997 | Diab et al. |
| 5,638,816 | A | 6/1997 | Kiani-Azarbayjany et al. |
| 5,638,818 | A | 6/1997 | Diab et al. |
| 5,645,440 | A | 7/1997 | Tobler et al. |
| 5,682,803 | A | 11/1997 | Boianjiu |
| 5,685,299 | A | 11/1997 | Diab et al. |
| 5,687,734 | A | 11/1997 | Dempsey et al. |
| 5,720,293 | A | 2/1998 | Quinn et al. |
| D393,830 | S | 4/1998 | Tobler et al. |
| 5,743,262 | A | 4/1998 | Lepper, Jr. et al. |
| 5,748,103 | A | 5/1998 | Flach et al. |
| 5,758,644 | A | 6/1998 | Diab et al. |
| 5,760,910 | A | 6/1998 | Lepper, Jr. et al. |
| 5,767,791 | A | 6/1998 | Stoop et al. |
| 5,769,785 | A | 6/1998 | Diab et al. |
| 5,782,757 | A | 7/1998 | Diab et al. |
| 5,785,659 | A | 7/1998 | Caro et al. |
| 5,791,347 | A | 8/1998 | Flaherty et al. |
| 5,810,734 | A | 9/1998 | Caro et al. |
| 5,823,950 | A | 10/1998 | Diab et al. |
| 5,830,131 | A | 11/1998 | Caro et al. |
| 5,833,618 | A | 11/1998 | Caro et al. |
| 5,841,435 | A | 11/1998 | Dauerer et al. |
| 5,860,919 | A | 1/1999 | Kiani-Azarbayjany et al. |
| 5,890,929 | A | 4/1999 | Mills et al. |
| 5,904,654 | A | 5/1999 | Wohltmann et al. |
| 5,919,134 | A | 7/1999 | Diab |
| 5,934,925 | A | 8/1999 | Tobler et al. |
| 5,940,182 | A | 8/1999 | Lepper, Jr. et al. |
| 5,987,343 | A | 11/1999 | Kinast |
| 5,995,855 | A | 11/1999 | Kiani et al. |
| 5,997,343 | A | 12/1999 | Mills et al. |
| 6,002,952 | A | 12/1999 | Diab et al. |
| 6,011,986 | A | 1/2000 | Diab et al. |
| 6,027,452 | A | 2/2000 | Flaherty et al. |
| 6,036,642 | A | 3/2000 | Diab et al. |
| 6,045,509 | A | 4/2000 | Caro et al. |
| 6,061,584 | A | 5/2000 | Lovejoy et al. |
| 6,067,462 | A | 5/2000 | Diab et al. |
| 6,074,345 | A | 6/2000 | Van Oostrom et al. |
| 6,081,735 | A | 6/2000 | Diab et al. |
| 6,088,607 | A | 7/2000 | Diab et al. |
| 6,110,522 | A | 8/2000 | Lepper, Jr. et al. |
| 6,124,597 | A | 9/2000 | Shehada |
| 6,128,521 | A | 10/2000 | Marro et al. |
| 6,129,675 | A | 10/2000 | Jay |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,253,097 | B1 | 6/2001 | Aronow et al. |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,285,896 | B1 | 9/2001 | Tobler et al. |
| 6,301,493 | B1 | 10/2001 | Marro et al. |
| 6,317,627 | B1 | 11/2001 | Ennen et al. |
| 6,321,100 | B1 | 11/2001 | Parker |
| 6,325,761 | B1 | 12/2001 | Jay |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,430,437 | B1 | 8/2002 | Marro |
| 6,430,525 | B1 | 8/2002 | Weber et al. |
| 6,440,067 | B1 | 8/2002 | DeLuca et al. |
| 6,463,311 | B1 | 10/2002 | Diab |
| 6,470,199 | B1 | 10/2002 | Kopotic et al. |
| 6,501,975 | B2 | 12/2002 | Diab et al. |
| 6,505,059 | B1 | 1/2003 | Kollias et al. |
| 6,515,273 | B2 | 2/2003 | Al-Ali |
| 6,519,487 | B1 | 2/2003 | Parker |
| 6,525,386 | B1 | 2/2003 | Mills et al. |
| 6,526,300 | B1 | 2/2003 | Kiani et al. |
| 6,541,756 | B2 | 4/2003 | Schulz et al. |
| 6,542,764 | B1 | 4/2003 | Al-Ali et al. |
| 6,544,173 | B2 | 4/2003 | West et al. |
| 6,544,174 | B2 | 4/2003 | West et al. |
| 6,580,086 | B1 | 6/2003 | Schulz et al. |
| 6,584,336 | B1 | 6/2003 | Ali et al. |
| 6,595,316 | B2 | 7/2003 | Cybulski et al. |
| 6,597,932 | B2 | 7/2003 | Tian et al. |
| 6,597,933 | B2 | 7/2003 | Kiani et al. |
| 6,606,511 | B1 | 8/2003 | Ali et al. |
| 6,632,181 | B2 | 10/2003 | Flaherty et al. |
| 6,639,668 | B1 | 10/2003 | Trepagnier |
| 6,640,116 | B2 | 10/2003 | Diab |
| 6,643,530 | B2 | 11/2003 | Diab et al. |
| 6,650,917 | B2 | 11/2003 | Diab et al. |
| 6,654,624 | B2 | 11/2003 | Diab et al. |
| 6,658,276 | B2 | 12/2003 | Kiani et al. |
| 6,661,161 | B1 | 12/2003 | Lanzo et al. |
| 6,671,531 | B2 | 12/2003 | Al-Ali et al. |
| 6,678,543 | B2 | 1/2004 | Diab et al. |
| 6,684,090 | B2 | 1/2004 | Ali et al. |
| 6,684,091 | B2 | 1/2004 | Parker |
| 6,697,656 | B1 | 2/2004 | Al-Ali |
| 6,697,657 | B1 | 2/2004 | Shehada et al. |
| 6,697,658 | B2 | 2/2004 | Al-Ali |

(56) References Cited

U.S. PATENT DOCUMENTS

| | | |
|---|---|---|
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,728,561 B2 | 4/2004 | Smith et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,790,178 B1 | 9/2004 | Mault et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,928,370 B2 | 8/2005 | Anuzis et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,949,380 B2 | 5/2011 | Fein et al. |

(56) References Cited

U.S. PATENT DOCUMENTS

| | | | |
|---|---|---|---|
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 2002/0007198 A1 | 1/2002 | Haupert et al. |
| 2002/0062070 A1 | 5/2002 | Tschupp et al. |
| 2002/0072880 A1 | 6/2002 | Svanerudh et al. |
| 2004/0204635 A1 | 10/2004 | Scharf et al. |
| 2005/0058486 A1 | 3/2005 | Yamanake |
| 2005/0075548 A1 | 4/2005 | Al-Ali et al. |
| 2005/0206518 A1 | 9/2005 | Welch et al. |
| 2006/0155576 A1 | 7/2006 | Deluz |
| 2006/0238333 A1 | 10/2006 | Welch et al. |

FOREIGN PATENT DOCUMENTS

| | | |
|---|---|---|
| EP | 0 313 238 A2 | 4/1986 |
| EP | 0 104 772 B1 | 3/1990 |
| EP | 0 640 978 | 3/1995 |
| EP | 1 281 353 A1 | 2/2003 |
| JP | 05-275746 A | 10/1993 |
| JP | 06-237013 A | 8/1994 |
| JP | 07-152553 | 6/1995 |
| WO | WO 88/10462 | 12/1988 |
| WO | WO 01/41634 A2 | 6/2001 |
| WO | WO 02/15781 | 2/2002 |
| WO | WO 03/073927 | 9/2003 |
| WO | WO 2004/060155 | 7/2004 |
| WO | WO 2005/040793 | 5/2005 |
| WO | WO 2006/023721 | 3/2006 |

OTHER PUBLICATIONS

Extended European Search Report, dated Mar. 22, 2012 for European Application No. EP 11 19 5281.8, filed Jul. 26, 2004, in 7 pages.

http://www.masimo.com/adt.htm, "Inop adt—Adult Disposable Digit Sensor," 1 page, reviewed on Sep. 17, 1999.

http://www.masimo.com/cables.htm, "Patient Cables", 1 page, reviewed on Sep. 17, 1999.

http://www.masimo.com/pndt.htm, "Products & Technology", 1 page, reviewed on Sep. 17, 1999.

http://www.masimo.com/systemo.htm, "System Overview & Performance", 2 pages, reviewed on Sep. 17, 1999.

http://www.mrequipment.com/products/oximetry_patient_mntrg.htm, "MR Equipment Magnetic Resonance Equipment Corporation, MR-Compatible High-Performance Optical Fiber Sensors, Pulse Oximetry Sensors for MRI Fiber Optic Sensors for use with MR-Compatible Pulse Oximeter", 2 pages, reviewed on Sep. 17, 1999.

International Search Report and Written Opinion for PCT/US2007/070362, dated Jun. 4, 2007.

Masimo Corporation, "Discrete Saturation Transforms Example", reviewed on Sep. 17, 1999.

MSP Industry Alert, Masimo to Introduce NR7 at ASA, pp. 18, 19, and the front and back cover, vol. 3, No. 3, Fall 2001

PCT International Search Report, App. No. PCT/US03/22712, App. Date: Jul. 18, 2001, 4 pages.

PCT International Search Report, App. No. PCT/US00/42637, App. Date Jul. 12, 2000, 5 pages.

PCT International Search Report, App. No. PCT/US04/23862, App. Date Jul. 26, 2004, 4 pages.

Reynolds, K.J., et al., "Temperature Dependence of LED and its Theoretical Effect on Pulse Oximetry", *British Journal & Anaesthesia*, 1991, vol. 67, pp. 638-643.

The International Search Report of PCT/EP2004/007042, mailed Sep. 23, 2004.

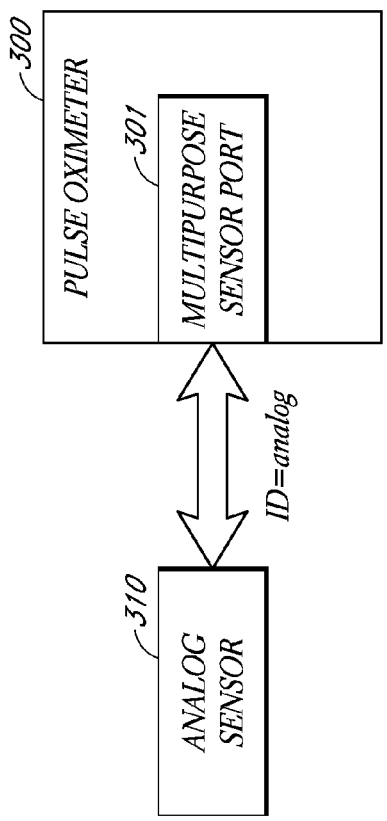
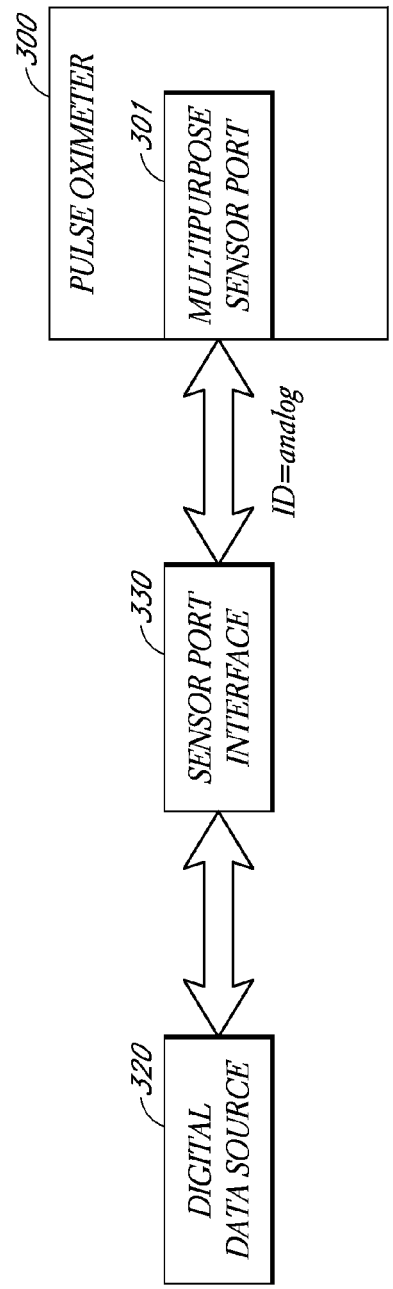

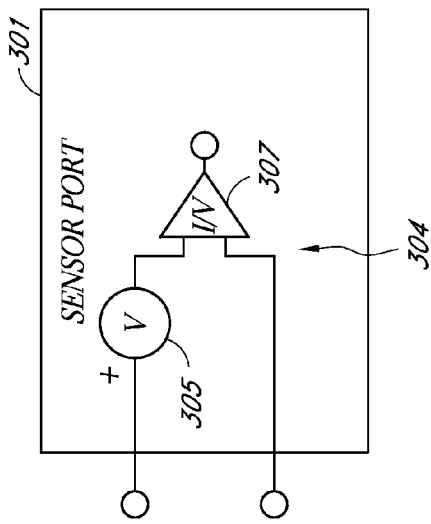
FIG. 3C
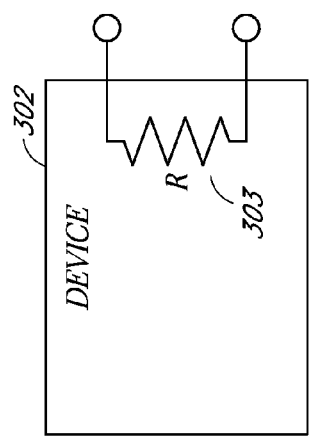
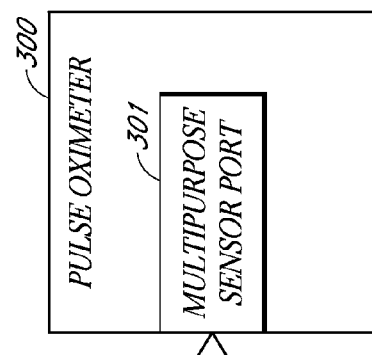
FIG. 3D

MULTIPURPOSE SENSOR PORT

REFERENCE TO RELATED APPLICATIONS

This application is a continuation of application Ser. No. 12/400,683, entitled "Multipurpose Sensor Port," filed Mar. 9, 2009, and application Ser. No. 12/400,683 is a continuation of application Ser. No. 10/898,680, entitled "Multipurpose Sensor Port," filed Jul. 23, 2004, and application Ser. No. 10/898,680 claims the benefit of U.S. Provisional Application No. 60/490,091 filed Jul. 25, 2003, entitled "Multipurpose Sensor Port." The present application incorporates the disclosure of both of the foregoing applications herein by reference.

BACKGROUND OF THE INVENTION

A pulse oximeter is a physiological instrument that provides noninvasive measurements of arterial oxygen saturation along with pulse rate. To make these measurements, a pulse oximeter performs a spectral analysis of the pulsatile component of arterial blood so as to determine the relative concentration of oxygenated hemoglobin, the major oxygen carrying constituent of blood. Pulse oximeters provide early detection of decreases in the arterial oxygen supply, reducing the risk of accidental death and injury. As a result, these instruments have gained rapid acceptance in a wide variety of medical applications, including surgical wards, intensive care units, general wards and home care.

FIG. 1 illustrates a pulse oximetry system 100 having a sensor 110 and a monitor 120. The monitor 120 may be a multi-parameter patient monitor or a standalone, portable or handheld pulse oximeter. Further, the monitor 120 may be a pulse oximeter 200, such as an OEM printed circuit board (PCB), integrated with a host instrument including a host processor 122, as shown. The sensor 110 attaches to a patient and receives drive current from, and provides physiological signals to, the pulse oximeter 200. An external computer (PC) 130 may be used to communicate with the pulse oximeter 200 via the host processor 122. In particular, the PC 130 can be used to download firmware updates to the pulse oximeter 200 via the host processor 122, as described below.

FIG. 2 illustrates further detail of the pulse oximetry system 100. The sensor 110 has emitters 112 and a detector 114. The emitters 112 typically consist of a red light emitting diode (LED) and an infrared LED that project light through blood vessels and capillaries underneath a tissue site, such as a fingernail bed. The detector 114 is typically a photodiode positioned opposite the LEDs so as to detect the emitted light as it emerges from the tissue site. A pulse oximetry sensor is described in U.S. Pat. No. 6,088,607 entitled "Low Noise Optical Probe," which is assigned to Masimo Corporation, Irvine, Calif. and incorporated by reference herein.

As shown in FIG. 2, the pulse oximeter 200 has a preamp 220, signal conditioning 230, an analog-to-digital converter (ADC) 240, a digital signal processor (DSP) 250, a drive controller 260 and LED drivers 270. The drivers 270 alternately activate the emitters 112 as determined by the controller 260. The preamp 220, signal conditioning 230 and ADC 240 provide an analog front-end that amplifies, filters and digitizes the current generated by the detector 114, which is proportional to the intensity of the light detected after tissue absorption in response to the emitters 112. The DSP 250 inputs the digitized, conditioned detector signal 242 and determines oxygen saturation, which is based upon the differential absorption by arterial blood of the two wavelengths projected by the emitters 112. Specifically, a ratio of detected red and infrared intensities is calculated by the DSP 250, and arterial oxygen saturation values are empirically determined based upon the ratio obtained. Oxygen saturation and calculated pulse rate values are communicated to the host processor 122 for display by the monitor 120 (FIG. 1). A pulse oximeter is described in U.S. Pat. No. 6,236,872 entitled "Signal Processing Apparatus," which is assigned to Masimo Corporation, Irvine, Calif. and incorporated by reference herein.

Further shown in FIG. 2, the pulse oximeter 200 has a sensor port 210 and a communications port 280. The sensor port 210 includes a connector and associated input and output signals and provides an analog connection to the sensor 110. In particular, the sensor port 210 transmits a drive signal 212 to the LED emitters 112 from the LED drivers 270 and receives a physiological signal 214 from the photodiode detector 114 in response to the LED emitters 112, as described above. The communication port 280 also includes a connector and associated input and output signals and provides a bi-directional communication path 282 between the pulse oximeter 200 and the host processor 122. The communication path 282 allows the DSP 250 to transmit oxygen saturation and pulse rate values to the monitor 120 (FIG. 1), as described above. The communication path 282 also allows the DSP firmware to be updated, as described below.

Additionally shown in FIG. 2, the pulse oximeter 200 has a micro-controller 290 and a flash memory 255. The flash memory 255 holds the stored program or firmware that executes on the DSP 250 to compute oxygen saturation and pulse rate. The micro-controller 290 controls data transfers between the DSP 250 and the host processor 122. In particular, to update the DSP firmware, the firmware is uploaded into the PC 130 (FIG. 1), which downloads the firmware to the host processor 122. In turn, the host processor 122 downloads the firmware to the micro-controller 290, which downloads it to the DSP 250. Finally, the DSP 250 writes the firmware to the flash memory 255.

SUMMARY OF THE INVENTION

To update the firmware in a pulse oximeter, particularly firmware on an OEM PCB integrated into a host instrument, requires a circuitous path using multiple protocols and multiple processors developed by different companies. Some of the protocols and processor interfaces are non-standard, requiring custom programming for different instruments. This is particularly problematic when the instruments are part of an installed base at various medical facilities. Further, some pulse oximeter products, such as handheld products, may not have a communications port for connecting to an external computer, and firmware upgrades would typically require returning the instrument to the factory.

Every pulse oximeter has a sensor port, which provides access to a DSP via one or more signal paths. Therefore, it is desirable to utilize a sensor port for downloading pulse oximetry firmware to the DSP. It is also desirable to provide this sensor port capability in existing instruments without hardware modification. Utilizing a sensor port in this manner would alleviate an instrument manufacturer from having to provide download communication capability between a host processor and an OEM PCB and would allow easy field upgrades of all instruments, including handhelds.

One aspect of a multipurpose sensor port is a physiological measurement method comprising a sensor port adapted to connect with an analog sensor, and a digital data source connected to the sensor port. An identifier associated with said data source is read, where the identifier is indicative that the data source is connected to the sensor port in lieu of the analog sensor. Digital data is then received over the sensor port. In one embodiment, the digital data is compiled in a signal processor. Where the digital data are instructions executable by the signal processor, the data may then be written from the signal processor into a firmware memory. The instructions may be uploaded to a PC, which is attached to a PC interface that is attached to the sensor port. Alternatively, the instructions are stored into a nonvolatile memory that is in communications with the sensor port. In another embodiment, the digital data is processed as a physiological signal.

Another aspect of a multipurpose sensor port is a physiological measurement system having a sensor port adapted to connect to a sensor and a data source. A reader is configured to identify which of the sensor and the data source is connected to the sensor port. A data path is configured to communicate an analog signal associated with the sensor and digital data associated with the data source to a signal processor according to the reader. In one embodiment, a firmware memory is configured to provide instructions to the signal processor. The signal processor is programmed to download the instructions from the data source and store the instructions in the memory. The instructions are executable by the signal processor so as to extract a physiological measurement from the analog signal. The data source may be a PC interfaced to the sensor port, where the instructions are uploaded to the PC. Alternatively, the data source is a nonvolatile memory adapted to communicate with the sensor port, where the instructions being stored in a nonvolatile memory.

In another embodiment, a first physiological measurement is derivable by the signal processor from the analog signal, and a second physiological measurement is derivable by the signal processor from the digital data. In yet another embodiment, a drive path is configured to communicate stored data associated with a physiological measurement to a digital device connected to the sensor port. The stored data may be trend data and/or log data maintained in memory that can be accessed by the signal processor. In a further embodiment, a drive path is configured to communicate acknowledgement data in conjunction with the communication of the digital data.

Yet another aspect of a multipurpose sensor port is a physiological measurement method where a drive path is provided that is adapted to activate emitters so as to transmit optical radiation through a fleshy medium having flowing blood. A signal path is provided that is adapted to communicate a detector response to the optical radiation after attenuation by the fleshy medium, where the response is indicative of optical characteristics of the flowing blood. Output digital data is transmitted over at least a portion of the drive path. In one embodiment, the output digital data is read from a memory having trend data and/or log data. In another embodiment, input digital data is received over at least a portion of the signal path, and receipt of that input digital data is acknowledged with the output digital data. In a particular embodiment, the input digital data is stored for use as signal processing instructions.

BRIEF DESCRIPTION OF THE DRAWINGS

FIGS. 3A-D are general block diagrams of a multipurpose sensor port connected to an analog sensor, a digital data source, or both;

DETAILED DESCRIPTION OF THE PREFERRED EMBODIMENT

Overview

Figure 1:
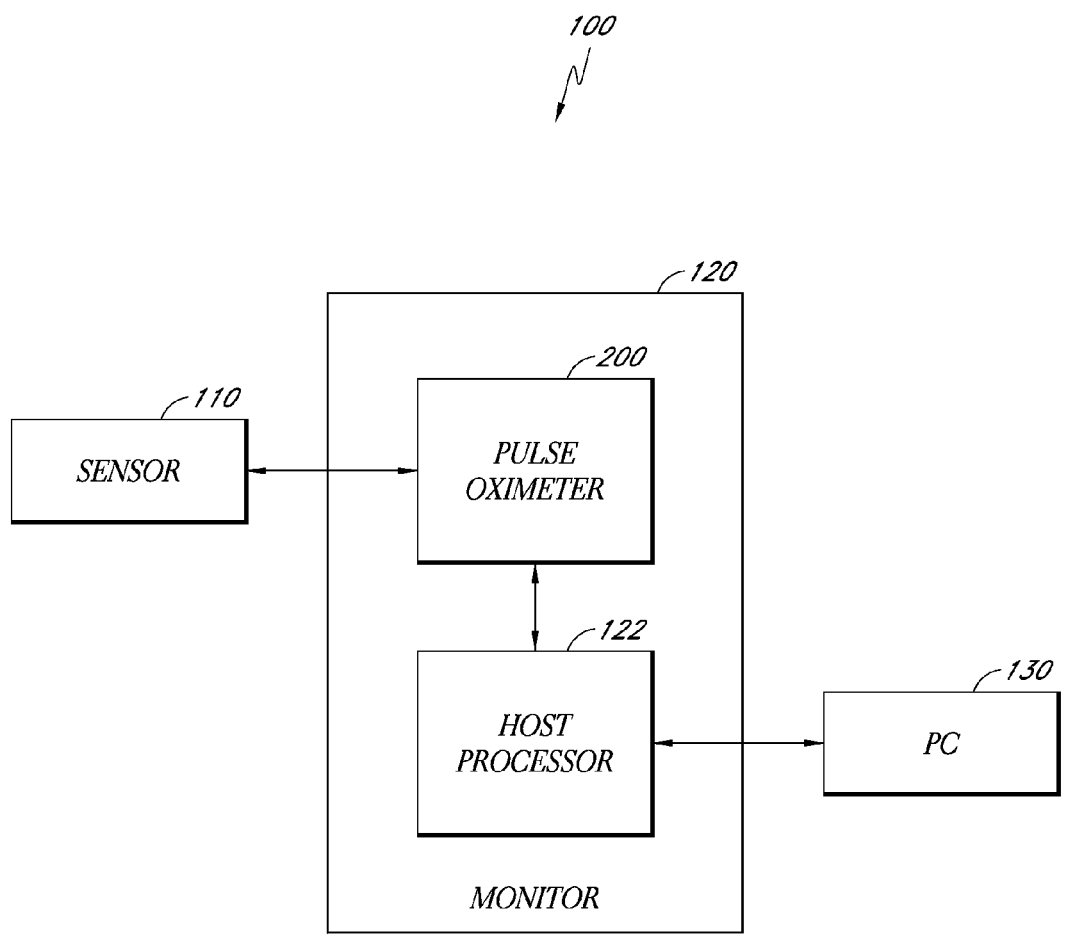
FIG. 1 is a general block diagram of a prior art pulse oximeter system utilizing an OEM printed circuit board (PCB)

FIGS. 3A-B illustrate a pulse oximeter 300 having a multipurpose sensor port 301 connected to an analog sensor 310 and a digital data source 320, respectively. As shown in FIG. 3A, if the pulse oximeter 300 determines that an analog sensor 310 is attached to the multipurpose sensor port 301, the multipurpose sensor port 301 is operated in an analog mode and functions as a typical sensor port, described above. As shown in FIG. 3B, if the pulse oximeter 300 determines that a digital data source 320 is attached to the multipurpose sensor port 301, the multipurpose sensor port 301 is operated in a digital mode and functions as a digital communications device. The data source 320 may connect to a sensor port interface 330 which, in turn, connects to the sensor port 301. The sensor port interface 330 may be used, for example, to present a standard communications interface, such as RS-232, to the data source 320. In one embodiment, when the pulse oximeter 300 is powered up, it reads an information element or other means of identification (ID) for the device connected to the sensor port 301. The ID identifies the device as either an analog sensor 310 or a data source 320. A sensor information element is described in U.S. Pat. No. 6,397,091 entitled "Manual and Automatic Probe Calibration," which is assigned to Masimo Corporation, Irvine, Calif. and incorporated by reference herein.

FIG. 3C illustrates a sensor port embodiment where a resistor value is a device ID. A resistor 303 is located in a device 302, which includes a sensor 310 (FIG. 3A), data source 320 (FIG. 3B) or interface 330 (FIG. 3B). The sensor port 301 has a reader 304 that measures the resistor value. The reader 304 includes a voltage source 305 and a current measurement device 307, such as a current-to-voltage converter. The voltage source 305 has a known voltage, which is applied to the resistor 303 when the device 302 is connected to the sensor port 301. The current measurement device 307 senses the magnitude of the resulting current flowing through the resistor 303 so as to determine the resistor value and, hence, the device ID.

FIG. 3D illustrates a pulse oximeter 300 having an analog sensor 310, a digital data source 320 and a switch 360 connected to a multipurpose sensor port 301. If the pulse oximeter 300 reads an ID that identifies mixed analog and digital, then the multipurpose sensor port 301 functions to transfer either an analog signal or digital data, as determined by the switch 360. The state of the switch 360 may be determined by the data source 320, the pulse oximeter 300 or both. In one embodiment, the pulse oximeter 300 transmits an identifiable waveform over an LED drive path 510 (FIG. 5) that is recognized by the switch 360 as a change state command. In this manner, the pulse oximeter 300 may occasionally receive digital data from, or transmit digital data to, the data source 320.

Applications

Figure 4:
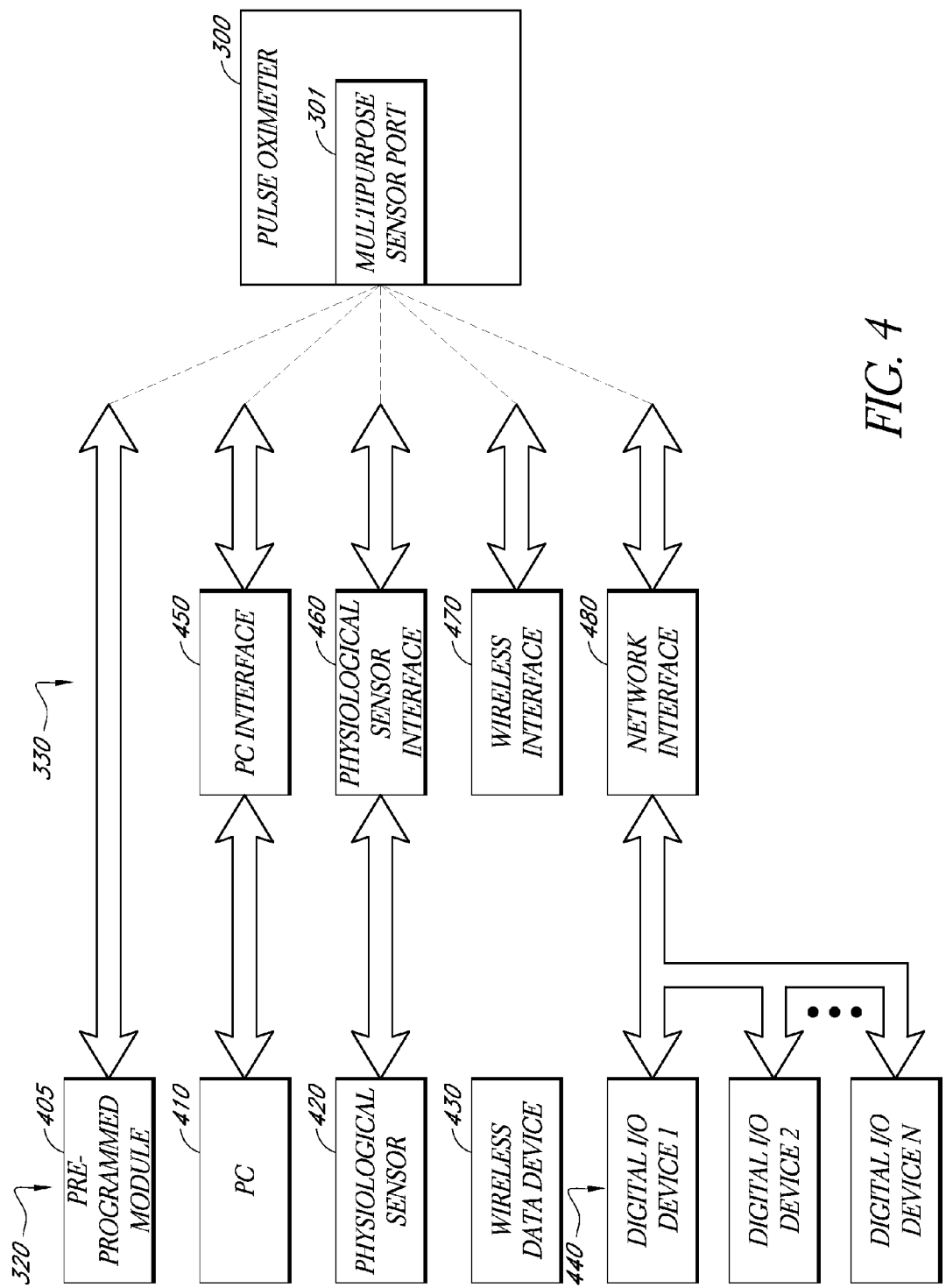
FIG. 4 is a general block diagram of a multipurpose sensor port having various digital data source inputs.

FIG. 4 illustrates various digital data source 320 and sensor port interfaces 330 that connect to a multipurpose sensor port 301. In one application, a preprogrammed module 405 connects directly to the sensor port 301. The module 405 has nonvolatile memory preprogrammed with, for example, upgrade firmware for the pulse oximeter 300. The module 405 also has the associated electronics to readout the memory data and communicate that data to the sensor port 301. In particular, the module 405 provides mechanical, signal level, and communication protocol compliance with the sensor port 301.

As shown in FIG. 4, in another application, a PC 410 connects to the sensor port 301 via a PC interface 450. For example, the PC 410 can be used to download firmware to the pulse oximeter 300, as described with respect to FIG. 5, below. As another example, the PC 410 can be used to upload information from the pulse oximeter 300, as described with respect to FIG. 6, below. In one embodiment, the PC interface 450 provides mechanical and signal level compliance with RS-232 on the PC side and mechanical and signal level compliance with the sensor port 301 on the pulse oximeter side, as described with respect to FIGS. 9A-B, below.

Also shown in FIG. 4, a physiological sensor 420 other than a conventional pulse oximeter sensor is attached to the multipurpose sensor port 301. A physiological sensor interface 460 drives the physiological sensor 420 and generates raw digital data to the sensor port 301. In this manner, a pulse oximeter 300 can be advantageously extended to provide physiological measurements in addition to oxygen saturation and pulse rate.

Further shown in FIG. 4, a wireless data device 430 is attached to the multipurpose sensor port 301 via a wireless interface 470. In this manner, the pulse oximeter can be advantageously extended to wireless data I/O and wireless networks. In one embodiment, the wireless interface 470 provides mechanical and signal level compliance with a wireless standard, such as IEEE-802.11, on one side and mechanical and signal level compliance with the sensor port 301 on the pulse oximeter side.

Additionally shown in FIG. 4, networked digital I/O devices 440 are attached to the multipurpose sensor port 301 via a network interface 480. In one embodiment, the network interface 480 provides mechanical and signal level compliance with a network standard, such as Ethernet, on one side and mechanical and signal level compliance with the sensor port 301 on the pulse oximeter side.

Firmware Upgrade Port

Figure 5:
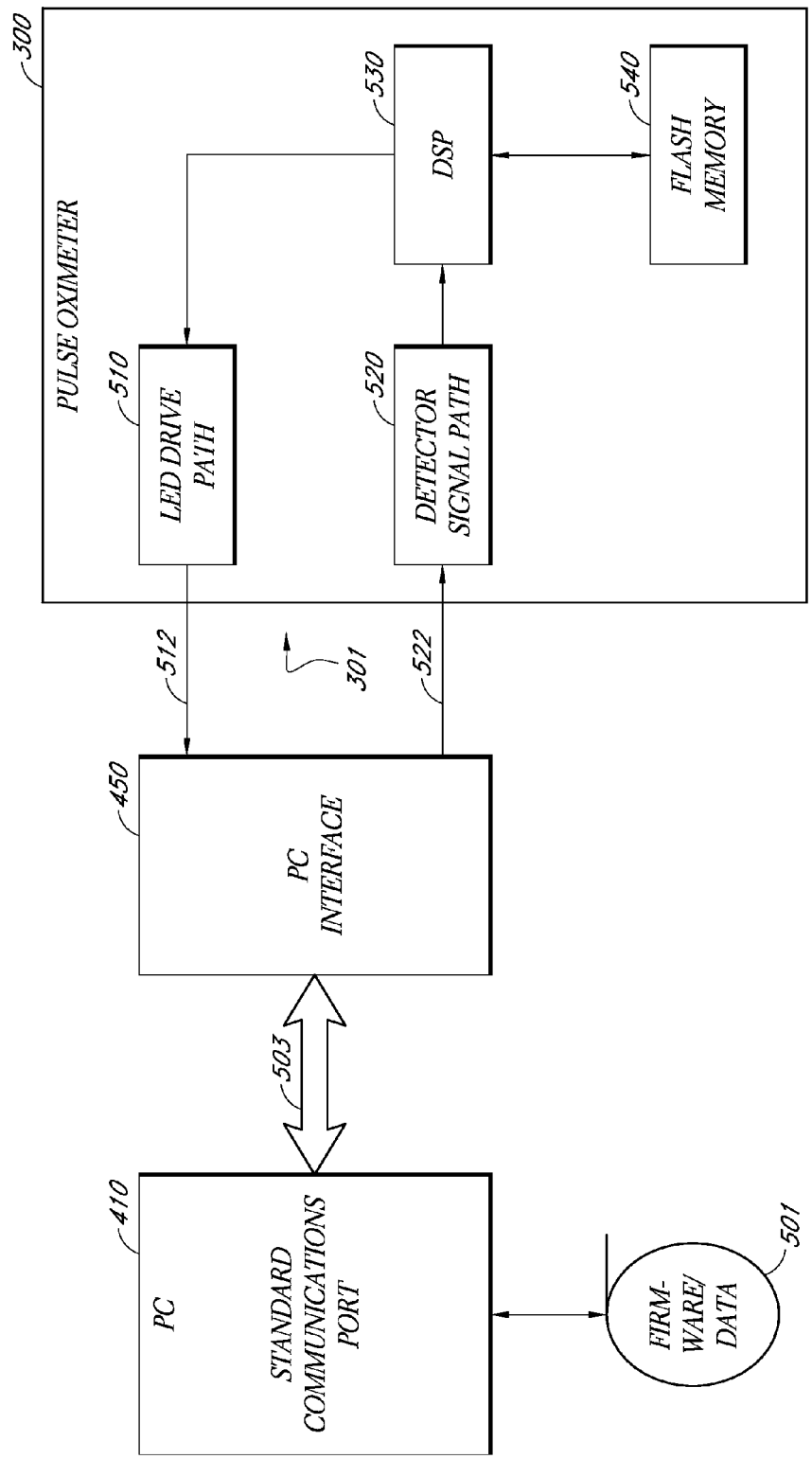
FIG. 5 is a block diagram of a multipurpose sensor port configured to download pulse oximeter firmware.

FIG. 5 illustrates a multipurpose sensor port 301 configured to download pulse oximeter firmware 501. The firmware 501 is uploaded to a PC 410 and downloaded over a standard communications bus 503 to a target pulse oximeter 300. The standard bus 503 may be, for example, RS-232, IEEE-488, SCSI, IEEE-1394 (FireWire), and USB, to name just a few. A PC interface 450 translates the signal levels on the sensor port 301 to the signal levels of the standard bus 503, and vice-a-versa. In particular, an output signal on the standard bus 503 is translated to a sensor port input signal 522, and a sensor port output signal 512 is translated to an input signal on the standard bus 503.

Figure 2:
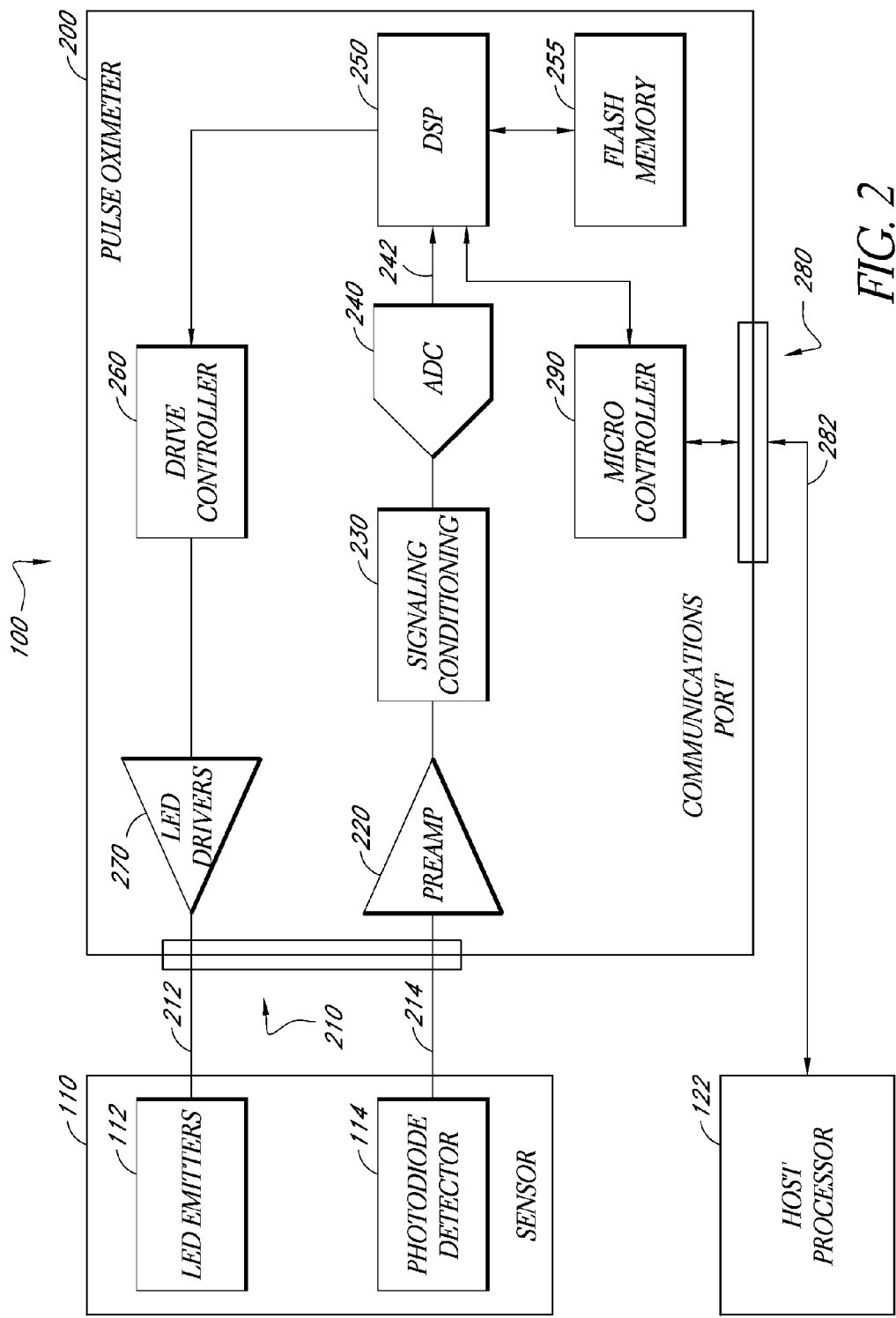
FIG. 2 is a detailed block diagram of a prior art pulse oximeter system.

As shown in FIG. 5, the pulse oximeter 300 has a detector signal path 520, a DSP 530, a flash memory 540 or other nonvolatile memory and a LED drive path 510, such as described with respect to FIG. 2, above. Data transmitted from the PC 410 is carried on the sensor port input 522, over the detector signal path 520 to the DSP 530, which loads the data into a flash memory 540. Acknowledgement data is transmitted from the DSP 530, over the LED drive path 510, and is carried on the sensor port output 512.

Figure 6:
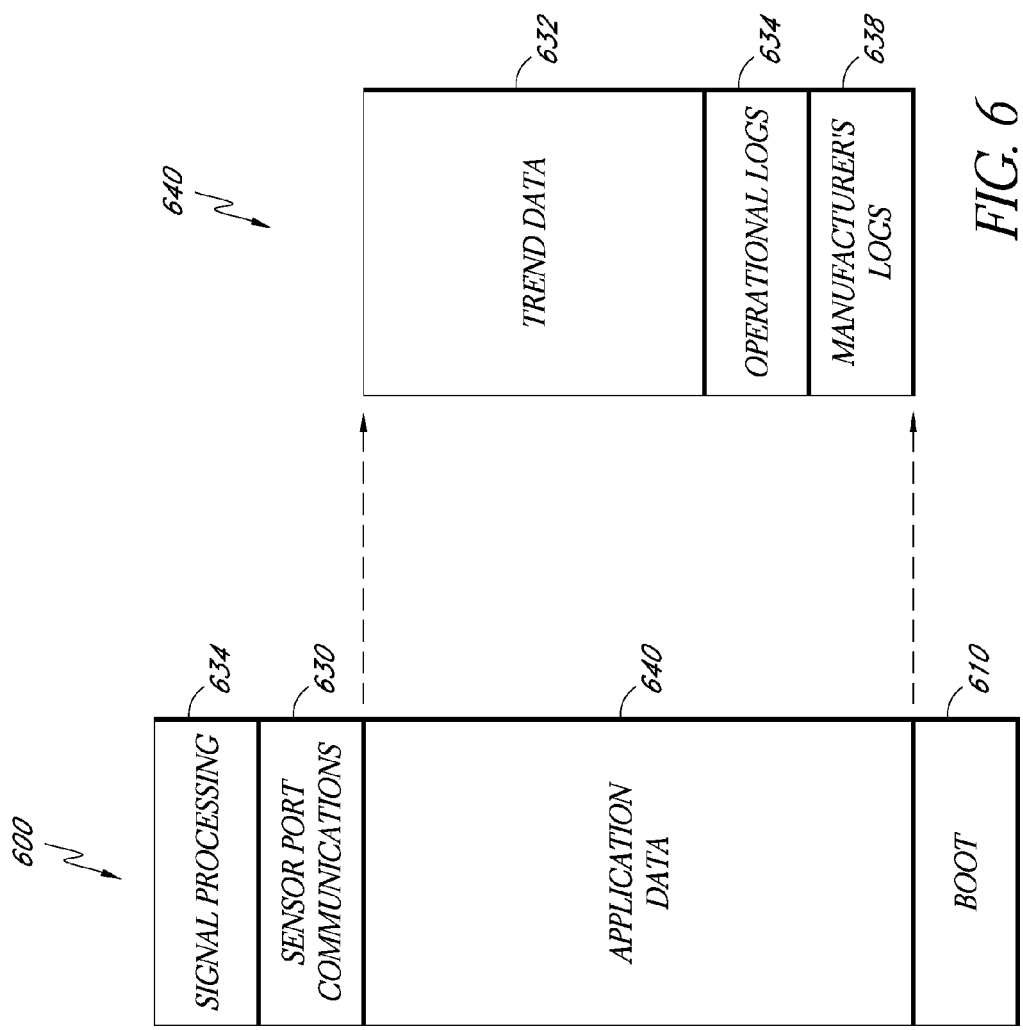
FIG. 6 is a DSP firmware memory map.

FIG. 6 illustrates a memory map 600 for the DSP flash memory 540 (FIG. 5). The memory map 600 illustrates partitions for DSP executable instructions such as boot firmware 610, signal processing firmware 620 and sensor port communications firmware 630 in addition to application data 640. The boot firmware 610 executes upon DSP power-up. The boot firmware 610 initializes the DSP and loads either the signal processing firmware 620 or the communications firmware 630 into DSP program memory, depending on the device ID, as described with respect to FIGS. 3A-D, above. The signal processing firmware 620 contains the oxygen saturation and pulse rate measurement algorithms, referred to with respect to FIGS. 1-2, above. The communications firmware 630 contains communications protocol algorithms, such as described with respect to FIG. 8, below. After completing its task of downloading firmware and/or uploading the applications data 640, the communications firmware 630 loads the signal processing firmware 620 so that the DSP can perform pulse oximetry measurements.

Also shown in FIG. 6, the application data 640 includes trend data 632, operational logs 634 and manufacturer's logs 638, which can be advantageously uploaded to a PC 410 (FIG. 5) or other digital device connected to the sensor port 301 (FIG. 5). Trend data 632 contains oxygen saturation and pulse rate measurement history. Operational logs 634 contain, for example, failure codes and event information. Failure codes indicate, for example, pulse oximeter board failures and host failures. Event information includes alarm data, such as the occurrence of probe off and low saturation events. Manufacturer's logs 638 contains, for example, service information.

Figure 7:
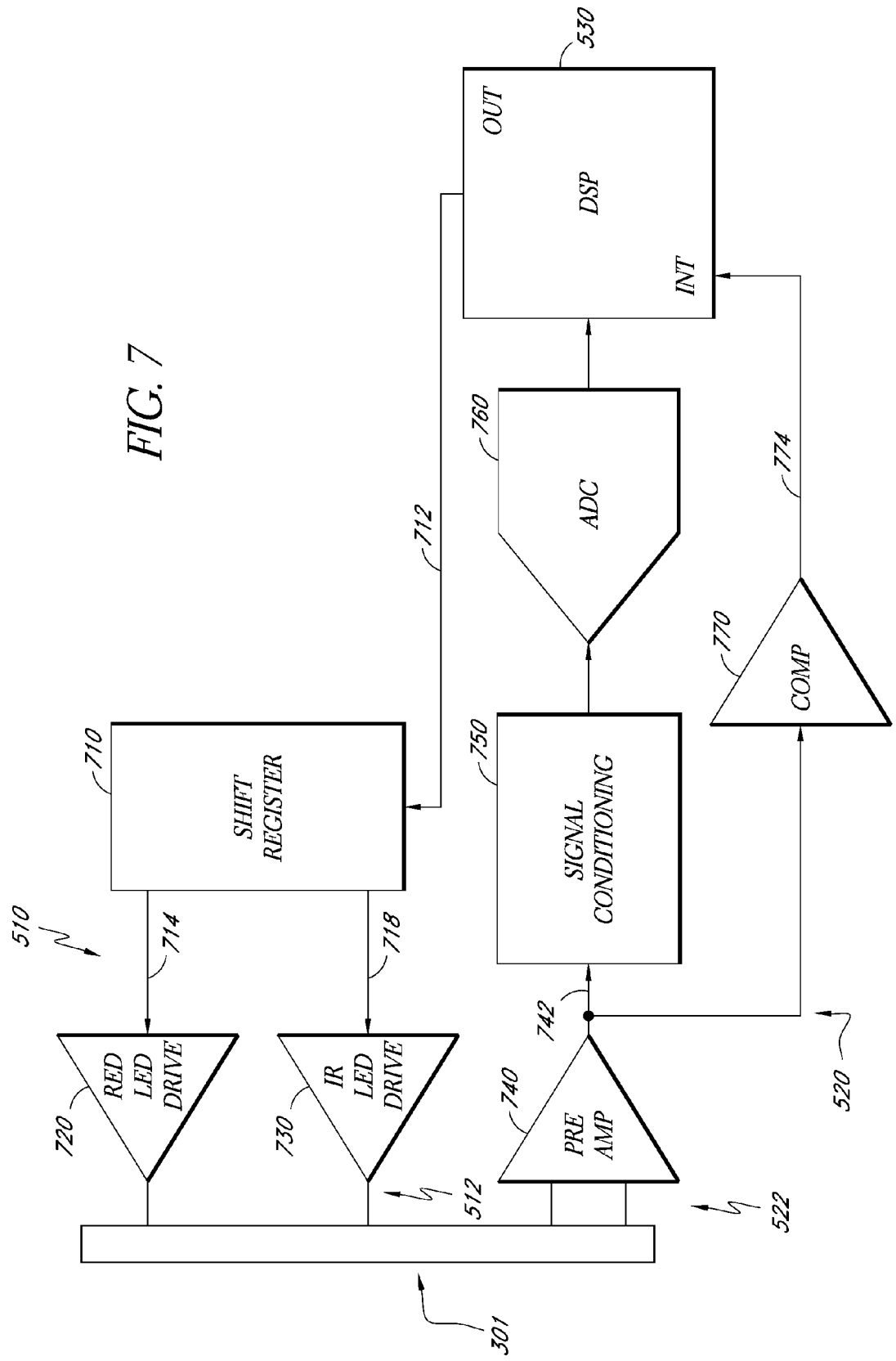
FIG. 7 is a detailed block diagram of a multipurpose sensor port embodiment and associated signal and data paths.

FIG. 7 illustrates a multipurpose sensor port embodiment 301 incorporating an LED drive path 510, a detector signal path 520 and a DSP 530, which function generally as described with respect to FIG. 5, above. The LED drive path 510 has a shift register 710, a red LED drive 720 and an IR LED drive 730. The shift register 710 has a data input 712, a red control output 714 and an IR control output 718. The DSP 530 provides serial control data on the shift register input 712 that is latched to the shift register outputs 714, 718 so as to turn on and off the LED drives 720, 730 according to a predetermined sequence of red on, IR on and dark periods. The detector signal path 520 has a preamp 740, signal conditioning 750 and an ADC 760 that perform amplification, filtering and digitization of the detector signal 522. The detector signal path 520 also has a comparator 770 that compares the preamp output 742 to a fixed voltage level and provides an interrupt output 774 to the DSP 530 accordingly. The comparator 770 allows the DSP to control the preamp voltage as a function of the level of the preamp signal output 742, as described in U.S. patent application Ser. No. 10/351,961 entitled "Power Supply Rail Controller," filed Jan. 24, 2003, which is assigned to Masimo Corporation, Irvine, Calif. and incorporated by reference herein. Advantageously, the comparator signal path also allows the DSP to accept serial digital data, as described with respect to FIG. 8, below.

Figure 8:
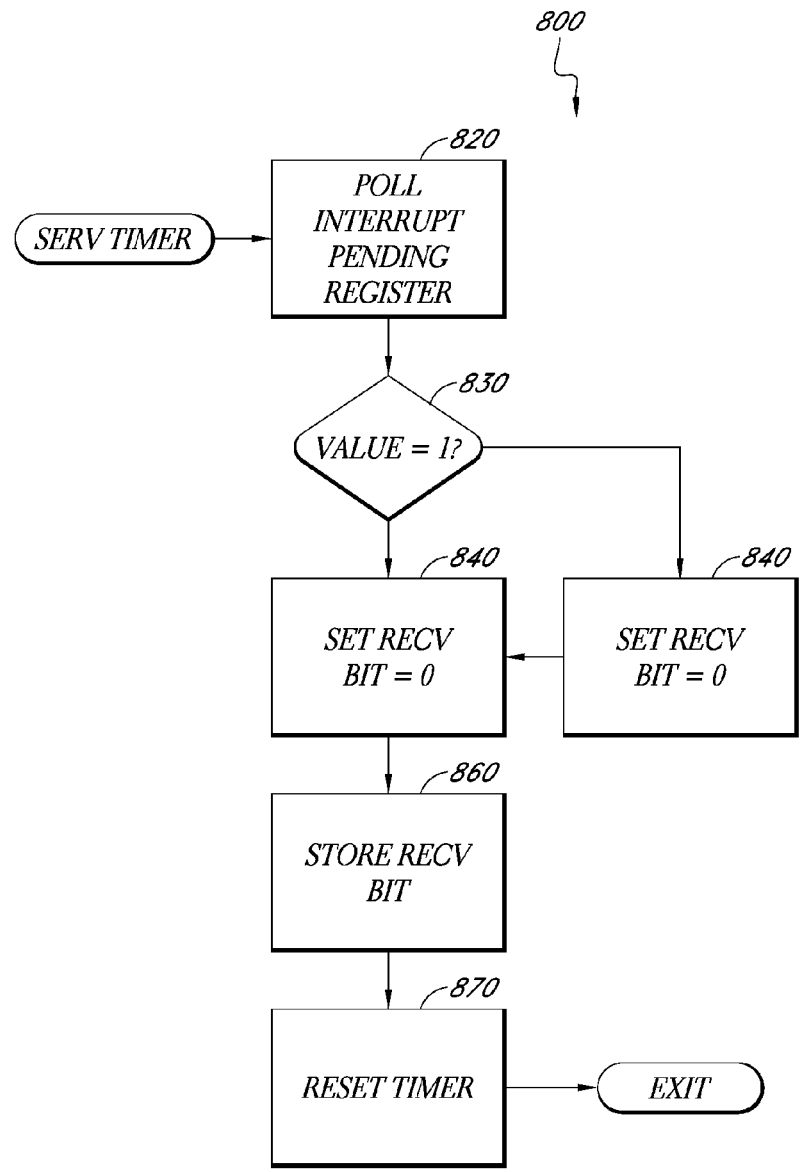
FIG. 8 is a flowchart of a digital data receiver routine.

FIG. 8 illustrates a serial data receiver 800 embodiment of one aspect of the communications firmware 630 (FIG. 6). The data receiver 800 utilizes the detector signal path 520 (FIG. 7) described above. A DSP internal timer is initialized to generate an interrupt at the incoming data baud rate. The timer interrupt periodically starts the data receiver 800 to determine and store a single bit. The data receiver 800 polls the status of the DSP interrupt input 774 (FIG. 7), which is initialized to be level-sensitive and disabled. Thus, whenever the comparator 770 (FIG. 7) is triggered, it will latch into a DSP interrupt pending register but will not generate an interrupt event. The timer service routine 800 polls the interrupt pending register 820. The pending register value is determined 830. If the value is a "1," then a zero bit has been received 840, else a one bit has been received 850. The received bit is stored 860 and the timer reset 870.

Figures 9, 9A:
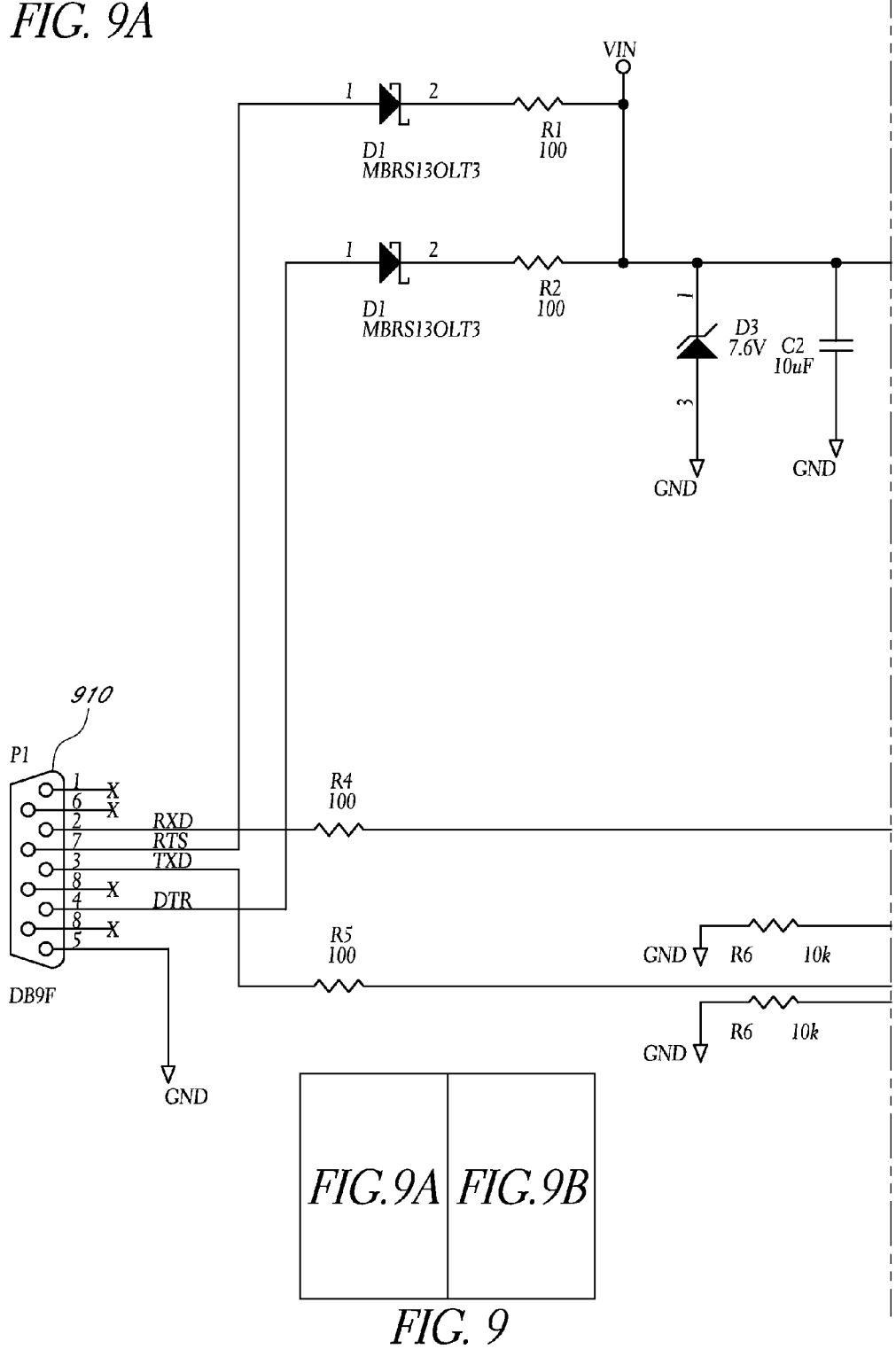
FIGS. 9A-B is a schematic of a RS232 interface for a multipurpose sensor port.
Figure 9B:
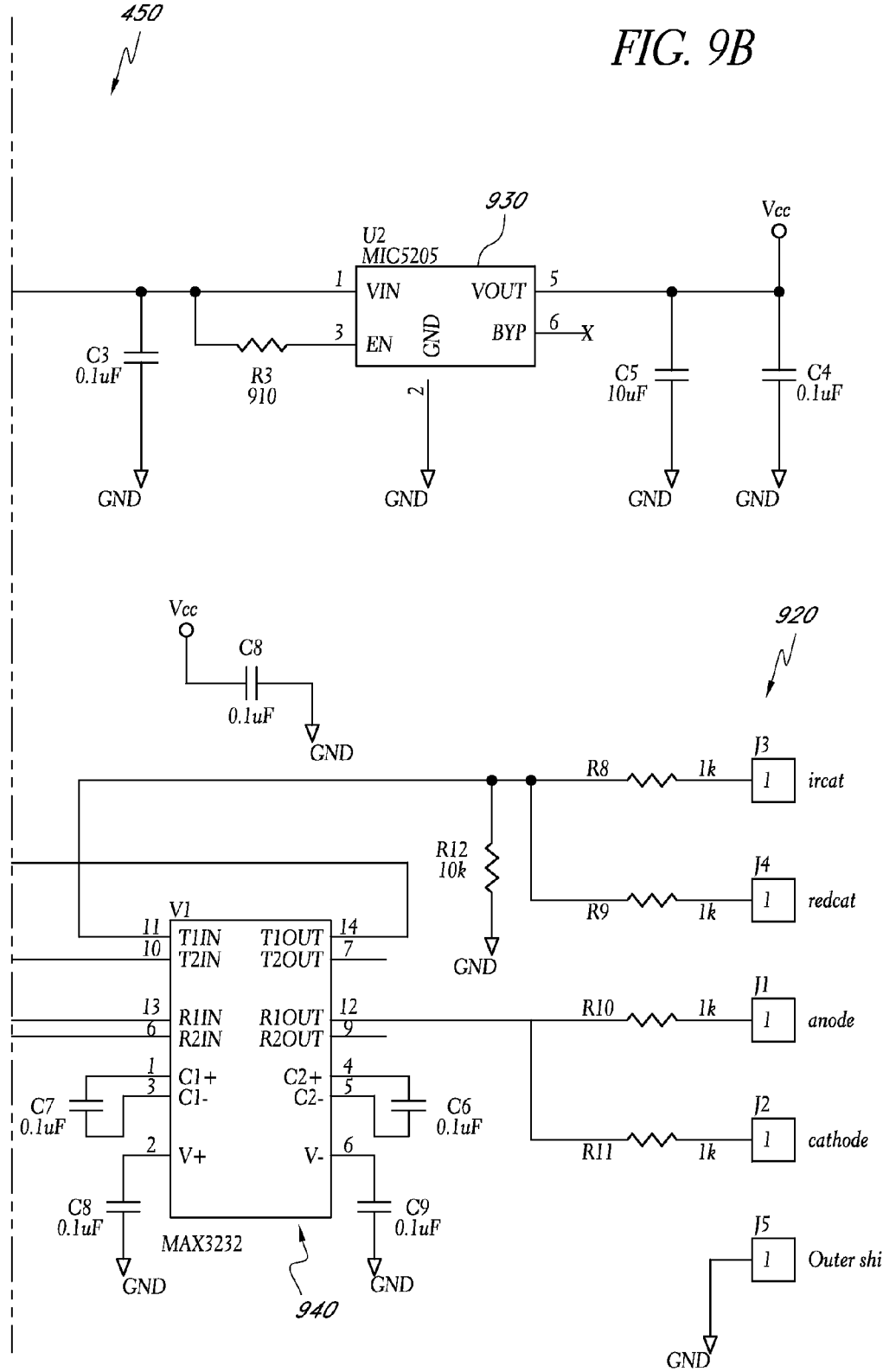

FIGS. 9A-B illustrate an RS-232 PC interface embodiment 450 having an RS-232 connector 910, a sensor connector 920, a voltage regulator 930 and a transceiver 940. The voltage regulator 930 draws power from either the RS-232 910 RTS (request to send) or DTR (data terminal ready) signal lines and provides regulated VCC power to transceiver 940. The transceiver 940 operates on either of the sensor 920 red or IR drive signal lines to generate an RS-232 910 RXD (receive data) signal. The transceiver 940 further operates on the RS-232 TXD (transmit data) signal line to generate a sensor 920 detector signal.

A multipurpose sensor port has been disclosed in detail in connection with various embodiments. These embodiments are disclosed by way of examples only and are not to limit the scope of the claims that follow. One of ordinary skill in the art will appreciate many variations and modifications.

What is claimed is:

1. A device configured to allow digital communication between a sensor port of a patient monitor and a digital data source external to the patient monitor and external to an analog physiological sensor, the device comprising:
    a first data path in electrical communication with a signal processor, and configured to communicate analog drive signals to the analog physiological sensor and digital data signals to the digital data source;
    a second data path in electrical communication with the signal processor, and configured to communicate analog signals indicative of light detected by said analog physiological sensor that has been attenuated by body tissue to the patient monitor and digital data signals from the digital data source to the patient monitor;
    a sensor port interface configured to provide mechanical and signal level compliance between said sensor port and said digital data source, said sensor port digitally communicating through said sensor port interface with said digital data source, said sensor port communicating said analog signals with said analog physiological sensor; and
    a reader configured to detect which of the analog physiological sensor and the data source is connected to the sensor port, said signal processor configured to receive an output from said reader and operate in an analog or digital mode responsive thereto.

2. The device of claim 1, wherein the digital data source comprises a preprogrammed memory module configured to deliver digital upgrade firmware data to the sensor port.

3. The device of claim 1 wherein the digital data source comprises a PC and wherein the sensor port interface is configured to provide signal level, mechanical, and communication protocol compliance to the output of the PC.

4. The device of claim 3 wherein the PC transmits upgrade firmware to the digital data interface, and wherein the sensor port interface is configured to translate the upgrade firmware from a standard PC output signal into a sensor port input signal and communicates the sensor input signal to the sensor port.

5. The device of claim 1 wherein the digital data source comprises a digital physiological sensor and wherein the sensor port interface is further configured to:
    communicate drive signals to the digital physiological sensor; and
    transmit digital data from the digital physiological sensor through the sensor port interface to the sensor port of the physiological measurement system.

6. A method of adapting communications between a patient monitoring device and either an analog physiological sensor or a digital data source, the method comprising:
    providing a sensor port of the patient monitoring device;
    detecting whether the analog physiological sensor or the digital data source is connected to the sensor port;
    when said analog physiological sensor is detected:
        transmitting analog drive signals to the analog physiological sensor,
        detecting light attenuated by body tissue using said analog physiological sensor, and
        communicating analog signals to the patient monitoring device indicative of the light that has been attenuated by body tissue; and
    when said digital data source is detected:
        transmitting digital data between the digital data source through a sensor interface to the sensor port
    wherein the analog signals and digital data are transmitted over the same data path between the sensor port and a signal processor of the patient monitoring device.

7. The method of claim 6 wherein transmitting digital data further comprises:
    transmitting upgrade firmware to the physiological monitor; and
    upgrading the firmware of the physiological monitor.

8. The method of claim 7 wherein transmitting digital data further comprises connecting the sensor port to a non-volatile memory module storing said upgrade firmware.

9. The method of claim 7 wherein transmitting digital data further comprises connecting the sensor port to a PC storing said upgrade firmware.

10. The method of claim 6 wherein transmitting digital data further comprises measurement data from said physiological monitor.

11. The method of claim 6 wherein transmitting digital data further comprises:
    connecting the sensor port to a PC; and
    providing signal level, mechanical, and communication protocol compliance to the output of the PC through the sensor port interface.

12. The method of claim 6 wherein the transmitting digital data further comprises:
    connecting a digital physiological sensor to the sensor port;
    communicating a drive signal through the interface to the physiological sensor; and
    generating raw digital data by means of the physiological sensor; and
    communicating the raw digital data through the interface to the sensor port of the physiological monitor.

13. The method of claim 6 wherein transmitting digital data further comprises connecting the sensor port to a wireless data device.

* * * * *

UNITED STATES PATENT AND TRADEMARK OFFICE
CERTIFICATE OF CORRECTION

PATENT NO.         : 8,920,317 B2                             Page 1 of 1
APPLICATION NO.    : 14/027019
DATED              : December 30, 2014
INVENTOR(S)        : Ammar Al-Ali et al.

It is certified that error appears in the above-identified patent and that said Letters Patent is hereby corrected as shown below:

In the Claims,

In Column 8, Line 27, in Claim 6, change "port" to --port;--.

In Column 8, Line 28, in Claim 6, change "and digital" to --and the digital--.

Signed and Sealed this
First Day of September, 2015

Michelle K. Lee
*Director of the United States Patent and Trademark Office*